(12) United States Patent
Banerjee et al.

(10) Patent No.: US 8,383,690 B2
(45) Date of Patent: Feb. 26, 2013

(54) PHARMACEUTICAL COMPOSITION USEFUL FOR THE TREATMENT OF PEPTIC ULCER DISEASES

(75) Inventors: Sukdeb Banerjee, Jadavpur (IN);
Pratap K. Das, Jadavpur (IN);
Suchandra Goswami, Jadavpur (IN);
Annalakshmi Chinniah, Jadavpur (IN);
Nilendu Panda, Jadavpur (IN);
Niranjan Prasad Sahu, Jadavpur (IN);
Basudeb Achari, Jadavpur (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 13/100,685

(22) Filed: May 4, 2011

(65) Prior Publication Data

US 2011/0207682 A1  Aug. 25, 2011

Related U.S. Application Data

(63) Continuation of application No. 11/705,476, filed on Feb. 12, 2007, now abandoned.

(30) Foreign Application Priority Data

Feb. 10, 2006 (IN) .............................. 369/DEL/2006

(51) Int. Cl.
*A61K 47/00* (2006.01)
*A01N 25/00* (2006.01)
(52) U.S. Cl. ......... 514/927; 514/925; 424/725; 424/778
(58) Field of Classification Search .................. 514/925, 514/927; 424/778, 725
See application file for complete search history.

(56) References Cited

U.S. PATENT DOCUMENTS 7,291,353 B2   11/2007   Das et al.

FOREIGN PATENT DOCUMENTS

WO   WO-03080095 A1   10/2003

*Primary Examiner* — Shaojia Anna Jiang
*Assistant Examiner* — Everett White
(74) *Attorney, Agent, or Firm* — Edwards Wildman Palmer LLP; David J. Silvia (57) ABSTRACT

The present invention deals with the pharmaceutical composition comprising the therapeutically effective amount of a compound oenothein C obtained from the bioactive fraction of plant *Woodfordia fruticosa* optionally along with one or more pharmaceutically acceptable carriers, additives, lubricants and diluents. Further it also provides a method of treating peptic ulcer diseases in a subject using the said pharmaceutical composition. It also relates to the use of the compound oenothein C in the treatment of peptic ulcer related diseases and a process for the isolation of the said compound.

13 Claims, 7 Drawing Sheets

Figure 1(a), 1(b) & 1(c) : HPLC profile of the Bioactive Fraction (1a), Methyl gallate (1b) and Oenothein C (1c)

Figure 2: Proton NMR of Oenothein C

Figure 3: ¹³C NMR of Oenothein C

Figure 4: Mass spectrum of Oenothein C

Figure 5: Proton NMR of Methyl gallate

Figure 7: Structure of Oenothein C and Methyl gallate

PHARMACEUTICAL COMPOSITION USEFUL FOR THE TREATMENT OF PEPTIC ULCER DISEASES

FIELD OF THE INVENTION

The present invention relates to a pharmaceutical composition comprising the therapeutically effective amount of the compound oenothein C optionally along with one or more pharmaceutically acceptable carriers, additives, lubricants and diluents.

More particularly, it relates to a method of treating peptic ulcer diseases in a subject using the said pharmaceutical composition.

Further, the present invention also relates to the use of a compound oenothein C in the treatment of peptic ulcer diseases including gastric ulcer, duodenal ulcer and also gastritis, gastro esophageal reflux disorder (GERD).

BACKGROUND AND PRIOR ART OF THE INVENTION

Peptic ulcer disease (PUD) is a broad classification encompassing different types of gastric and duodenal ulcers, all of which are clinically characterized as an erosion of the mucosal lining in one or more areas of gastrointestinal tract. PUD does not occur when there is a balance between the aggressive factors and the defensive factors, manifesting only when the former factors become stronger than normal or when the latter factors weaken [1]. However, it is now accepted that *Helicobacter pylori* is present in more than 90% of duodenal ulcers and 70-80% of gastric ulcers [2]. PUD is therefore currently treated as an infectious disease also, cured with antibiotics.

Two of the major etiologies of peptic ulcer diseases are hyperacid secretion and infection by pathogenic *H. pylori*. For ulcers that are not caused by *H. pylori*, acid suppressive therapy alone is recommended either in the form of $H_2$ receptor antagonists or proton pump inhibitors, beside simple use of acid neutralizing agents like antacids. However, antibiotic therapy should always be combined with acid suppressive therapy when treating *H. pylori*. Thus, the current therapeutic regimen for PUD with *H. pylori* involves two antibiotics, one antisecretory drug and one mucus coating agent (quadruple therapy) consisting of suitable four agents among amoxycillin, tetracycline, clarithromycin, metronidazole, and sucralfate or bismuth subsalicylate or subcitrate along with either of the two acid suppressing agents, $H_2$ receptor blocker or proton pump inhibitor [3]. However, as with most drugs, a number of side effects are involved in their use. The adverse drug interaction of the cytochrome P450 system with $H_2$ receptor blocker, hypersensitivity and damage of the liver by proton pump inhibitors, requirements of multiple doses of antacids to alleviate symptomatic-only relief, and the development of antibiotic resistance, coupled with ulcer recurrence problems [4] necessitate searching for better therapeutic management of PUD. For the development of effective anti ulcer agents having low toxicity, the inventors investigated a wide range of Indian medicinal plants. As a result, *Woodfordia fruticosa* flowers and its extracts were found to have low toxicity and excellent anti ulcer activity, and thus the present invention is completed, co-pending patent applications (WO 03/080095 PCTIN/03/0067) and US patent 20060040005, describing anti peptic ulcer activity of an extract of the plant flower *W. fruticosa* [5], delineating a new active principle, oenothein C.

*Woodfordia fruticosa* Kurz (syn. *W. floribunda* Salisb.) belongs to the family Lythraceae. English names that are frequently used for the plant are Fire Flame Bush and Shiranjitea. The local and traditional names are innumerable, especially in India, because of widespread traditional use. In India, a few popularly known names are Dhataki, Dawi, Jargi, Dhai, Harwari, Phulsatti, Dhavdi etc [6, 7]. The plant *W. fruticosa* is abundantly present throughout India, ascending up to an altitude of about 1500 meters. It is also present in a majority of the countries of South East and Far East Asia like Malaysia, Indonesia, Sri Lanka, China, Japan and Pakistan as well as Tropical Africa [8].

This plant has long been in regular demand amongst practitioners of traditional medicines throughout India and in different Southeast Asian countries. In India, it is a much-used medicinal plant in Ayurvedic and Unani systems of medicines [8-13]. Although all parts of this plant possess valuable medicinal properties, there is a heavy demand for the flowers, both in domestic and international markets specialized in the preparation of herbal medicines [14].

According to the Indian Systems of Medicine, this flower is pungent, acrid, cooling, toxic, alexiteric, uterine sedative, and anthelmintic, and useful in thirst, dysentery, leprosy, erysipelas, blood diseases, leucorrhoea, menorrhagia and toothache [8-19]. Many marketed drugs comprise flowers and other parts of the plant [11, 16-18]. The flowers are being used in the preparation of Ayurvedic fermented drugs called 'Arista's and 'Asava's [9, 19], and very popular in the Indian subcontinent as also in other south Asian countries [20, 21]. These flowers are capable of setting alcoholic fermentation as normally achieved by the use of pure yeast culture [9, 19]. A popular crude drug (called 'Sidowaya' or 'Sidawayah') of Indonesia and Malaysia chiefly contains dried flowers of *W. fruticosa* [22]. It is also an ingredient of a preparation used to make barren women fertile [22,23].

A systematic phytochemical investigation of *W. fruticosa* flowers described the characteristic presence of about 22% of tannin and also saponins in the aqueous and alcohol extracts [6]. Existence of triterpenoids besides steroids & steroid-like molecules, alkaloids and flavonoids was reported from the less polar solvent extracts [6, 7, 24, 25]. The presence of quercetin-3-rhamnoside, 2-hydroxy-1:4-naphthaquinone, polyphenols and traces of alkaloids was described [24-29]. Ellagic acid was isolated as the major polyphenol from the flowers and leaves [30]. Other polyphenols isolated include polystachoside, myricetin-3-galactoside and pelargonidin-3, 5-diglucoside, the last one being the scarlet-red pigment that confers the beautiful colour to the flower [30]. A series of macrocyclic hydrolysable tannins—monomeric, dimeric as well as trimeric—have so far been isolated and their structures elucidated by spectral and chemical evidence [31-34].

Systematic pharmacological and biochemical investigations of the traditional remedies based on the plant and its parts substantiated many of the earlier empirical observations. Traditionally, fermented Ayurvedic drugs known as 'Arishta's are very popular in Southeast Asian countries. They are used for the treatment of a wide variety of diseases. In the preparations of many 'Arishta's, dried flowers of *W. fruticosa* are being used to enhance sucrose hydrolysis [35]. Immunomodulatory activity of the Ayurvedic drug 'Nimba Arishta', which contains *W. fruticosa* flowers, was demonstrated. Substantial increase in the inhibition of both human complement activity and chemoluminiscence generated by zymogen-stimulated human polymorphonuclear leukocytes was observed. Such increased biological activity was attributed to the immunoactive constituents released from the flowers of *W. fruticosa* [36]. An Ayurvedic medicine called ' Balarishta', a drug of 'Asava' and ' Arishta' group, contains *W. fruticosa* flower as one of the major constituents and is indicated in burning sensation (Agnimandya), weakness (Daurbalya) and rheumatic diseases (Vataja roga) [37]. This multi-ingredient Ayurvedic medicine, widely prescribed for the treatment of rheumatism, has exhibited anti-inflammatory activity against cotton pellet induced granuloma in albino rats. Activities of marker enzymes like acid phosphatase, GPT (glutamate pyruvate transaminase) and GOT (glutamate oxaloacetate transaminase) were significantly lowered by such Ayurvedic preparations, as compared with the reference anti-inflammatory drug phenylbutazone [38]. The aqueous extract of the flowers is recorded as a uterine sedative having usefulness in leucorrhea and menorrhagia [6, 39]. Anti-leucorrhoeic property of an Ayurvedic preparation containing *W. fruticosa* was shown to be effective in dysfunctional uterine bleeding [40].

New-biology based preclinical observations of some of the complex macromolecules, isolated from the flowers as well as leaves of *W. fruticosa*, are increasingly becoming available in recent time. Woodfordin C, a macrocyclic dimeric hydrolysable tannin isolated from the methanol extract of the leaves [33], showed remarkable inhibition of DNA topoisomerase II in vitro and antitumor activity in vivo [41]. Anti tumor activity of woodfordin C and oenothein B was evaluated in human carcinoma cell lines and in sarcoma 180 tumor-bearing ICR mice [42]. The macrocyclic ellagitannins inhibited the viability of S-180 tumor cells in vitro as well as in vivo. The cytotoxic effect in cell culture was demonstrated to be selective, and is perhaps expressed through potentiation of host-immune defense system, like activation of NK cells and/or augmentation of interleukin secretion [42, 43]. Woodfordin I has recently been shown to induce apoptosis in human chronic myelogenous leukemia (CML) K 562 cells. It suppressed proliferation of and induced apoptosis in these CML cells, as judged by cytomorphology, internucleosomal DNA fragmentation and externalization of phosphatidyl serine. Several naturally occurring polyphenolic compounds, including flavonoids, anthraquinones and certainly macrocyclic ellagitannins, isolated from *W. fruticosa* as well as from other medicinally useful plants, inhibited LPS-induced iNOS and COX-2 gene expression, implying their putative role in the management of inflammation [44, 45].

Patents describing the invention of anti ulcer agents from plant extracts like *Psoralae corylifolia* [46], *Panax* genus [47] or polyherbal preparations [48, 49] have been disclosed. The use of the plant *Woodfordia fruticosa* in various traditional systems of medicine, and also the effects of several components contained therein, as reviewed above, led to a few patents dealing with management of gynecological and hyperandrogenic disorders [50, 51] or bronchial asthma [52]. Skin whitening cosmetics containing *W. fruticosa* plant extract has been disclosed in a Japanese patent [53].

PUD is a specific pathological condition for which the acid HCl and the bug *H. pylori* are accepted to be the two major etiologies for the pathogenesis of gastroduodenal ulcers. Because of the failure of the current medical management after using even quadruple therapy (clarithromycin, amoxycillin, proton pump inhibitor or $H_2$ receptor blocker, and sucralfate) in terms of ulcer recurrence and antibiotic resistance, a non-toxic and effective natural medicament is needed for the simultaneous treatment of gastric as well as duodenal ulcers.

DISCLOSURE OF THE INVENTION

Accordingly, the present invention has endeavored to develop a pharmaceutical composition comprising a therapeutically effective amount of a compound oenothein C, isolated by a bioassay guided fractionation technique from the aqueous-methanolic (50%) extract of the plant flower *Woodfordia fruticosa*, that would effectively treat peptic ulcer diseases for which the acid HCl and the bug *H. pylori* are the two major pathological reasons.

OBJECTS OF THE INVENTION

The main object of the present invention is to provide a pharmaceutical composition useful for the treatment of the peptic ulcer diseases.

Another object of the present invention is to provide a method of treating peptic ulcer diseases in a subject using the said pharmaceutical composition.

Further, another object of the present invention is to provide the use of a compound oenothein C in the treatment of peptic ulcer diseases including gastric ulcer, duodenal ulcer and also gastritis, gastro esophageal reflux disorder (GERD).

Yet another object of the present invention is to provide a safe compound oenothein C useful in the treatment of various diseases relating to peptic ulcer including gastric ulcer, duodenal ulcer and also gastritis, gastro esophageal reflux disorder (GERD).

SUMMARY OF THE INVENTION

Accordingly the present invention deals with the pharmaceutical composition comprising the therapeutically effective amount of a compound oenothein C obtained from the bioactive fraction of plant *Woodfordia fruticosa* optionally along with one or more pharmaceutically acceptable carriers, additives, lubricants and diluents. Further it also provides a method of treating peptic ulcer diseases in a subject using the said pharmaceutical composition. It also relates to the use of the compound oenothein C in the treatment of peptic ulcer related diseases and a process for the isolation of the said compound.

In an embodiment of the present invention, a pharmaceutical composition useful for the treatment of the peptic ulcer diseases, wherein the said pharmaceutical composition comprising the therapeutically effective amount of the compound oenothein C or optionally along with one or more pharmaceutically acceptable carriers, additives, lubricants and diluents.

In another embodiment of the present invention, the pharmaceutical composition useful for the treatment of the peptic ulcer diseases, comprising, compound oenothein C which is obtained from the bioactive fraction of plant *Woodfordia fruticosa*.

In yet another embodiment of the present invention, the pharmaceutical composition has carriers selected from the group consisting of proteins, carbohydrates, sugar, magnesium stearate, cellulose, calcium carbonate, starch-gelatin paste and pharmaceutically acceptable carriers, excipients, diluents or solvents.

In still another embodiment of the present invention the pharmaceutical composition wherein the compound oenothein C is administered at a dose of 0.005 mg/Kg body weight/day to 0.5 mg/Kg body weight/day.

In an embodiment of the present invention, the pharmaceutical composition wherein the compound oenothein C is preferably administered at a dose of at least 0.05 mg/Kg body weight/day.

In another embodiment of the present invention, the pharmaceutical composition wherein the compound oenothein C does not show any toxic effect at the single dose level up to 250 mg/kg body weight.

In yet another embodiment of the present invention, the administration route for the said composition used is selected from the group comprising oral, intramuscular, intravenous administration.

In still another embodiment of the present invention, the composition is used in the form selected from the group comprising of powder, injectable, syrup, capsule, tablet.

In an embodiment of the present invention, the composition is useful in the treatment of peptic ulcer diseases selected from the group comprising of gastric ulcer, duodenal ulcer and also gastritis, gastro esophageal reflux disorder (GERD).

In another embodiment of the present invention, the pharmaceutical composition wherein the compound oenothein C has dual functions in terms of anti gastric proton pump and anti *Helicobacter pylori* activity.

In yet another embodiment of the present invention, the pharmaceutical composition wherein the compound oenothein C inhibits gastric proton pump activity in vitro in the concentration range from 0.13 to 1.3 μM wherein the $IC_{50}$ value is 0.6 to 0.8 μM.

In still another embodiment of the present invention, the pharmaceutical composition wherein the compound oenothein C shows bacteriostatic as well as bactericidal activity against clinical as well as standard strains of *Helicobacter pylori*.

In an embodiment of the present invention, the pharmaceutical composition wherein the compound oenothein C shows the bacteriostatic activity against *Helicobacter pylori* with minimum inhibitory concentration (MIC) in the range of 6.25 μg/mL to 25.0 μg/mL.

In another embodiment of the present invention, the pharmaceutical composition wherein the compound oenothein C shows the bactericidal activity against *Helicobacter pylori* with minimum bactericidal concentration (MBC) in the range of 25.0 μg/mL to 50.0 μg/mL.

In yet another embodiment of the present invention, the compound oenothein C inhibits specifically *H. pylori* only, and does not inhibit other aerobic bacteria, as evident from higher MIC values (>400 μg/mL) against gram positive and gram negative bacteria.

BRIEF DESCRIPTION OF THE FIGURES AND TABLES

FIG. 1 (a) represents the HPLC profile of the bioactive fraction obtained from the plant *Woodfordia fruticosa*.

FIG. 1 (b) represents the HPLC profile of the compound methyl gallate obtained from the Bioactive Fraction of the plant *Woodfordia fruticosa*. It showed a single peak corresponding to one of the major peaks in the original Bioactive Fraction.

FIG. 1 (c) represents the HPLC profile of the compound oenothein C obtained from the Bioactive Fraction of the plant *Woodfordia fruticosa*. It showed a single peak corresponding to one of the major peaks in the original Bioactive Fraction. The relative abundance (yield %) of oenothein C in the Bioactive Fraction was determined to be 0.008%.

Figure 2:
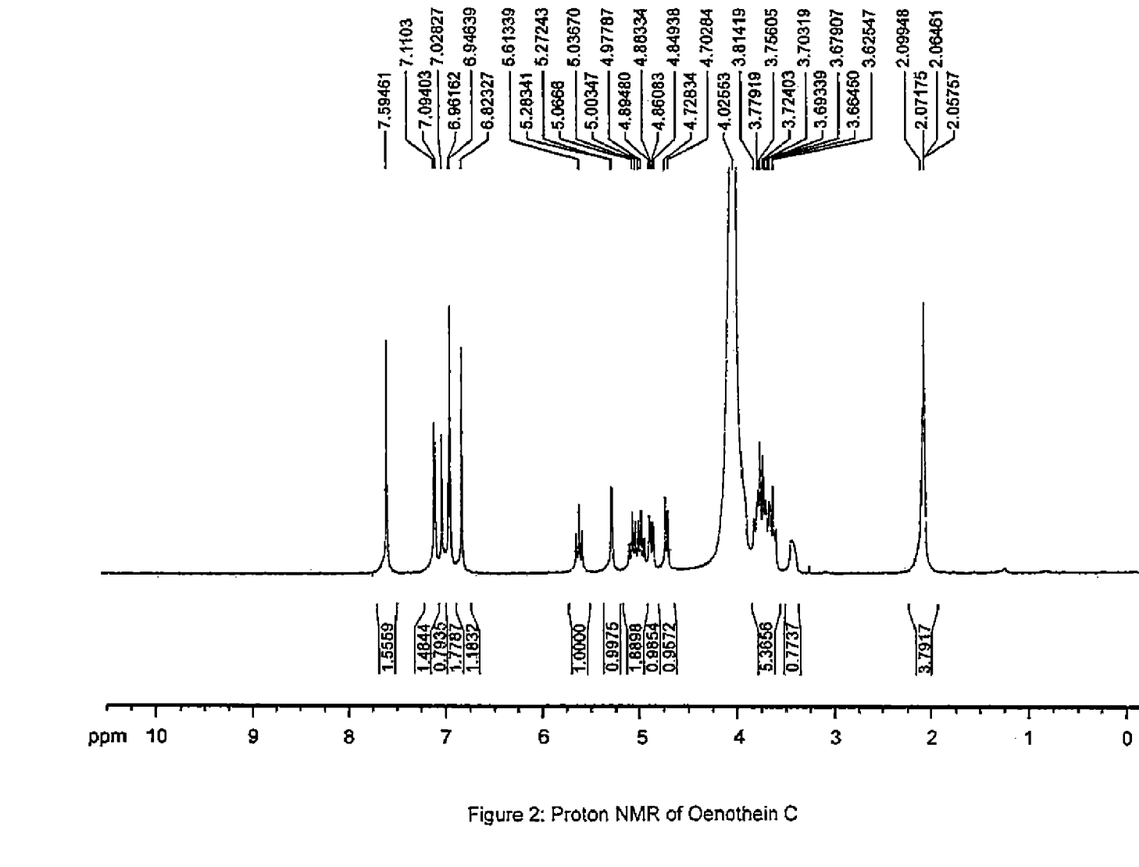
FIG. 2 represents the proton NMR of the compound oenothein C.
Figure 3:
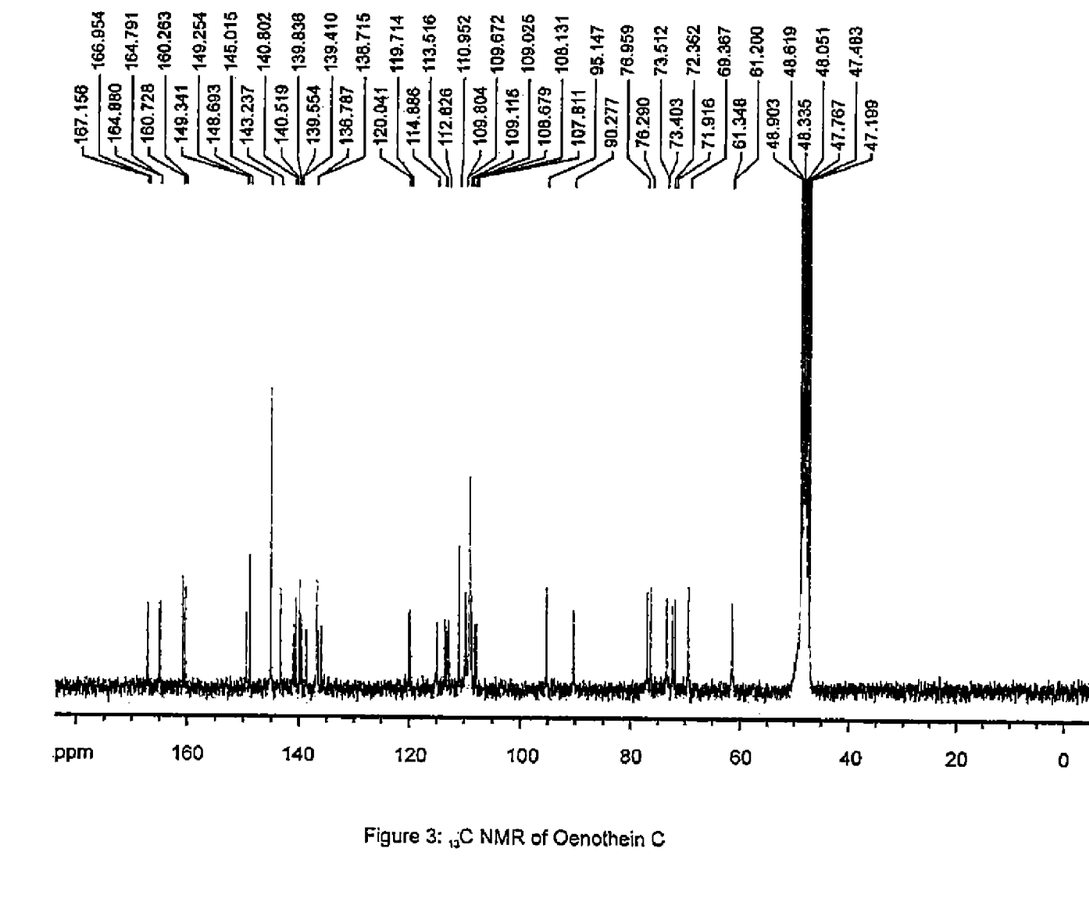
FIG. 3 represents the $^{13}C$ NMR of the compound oenothein C.
Figure 4:
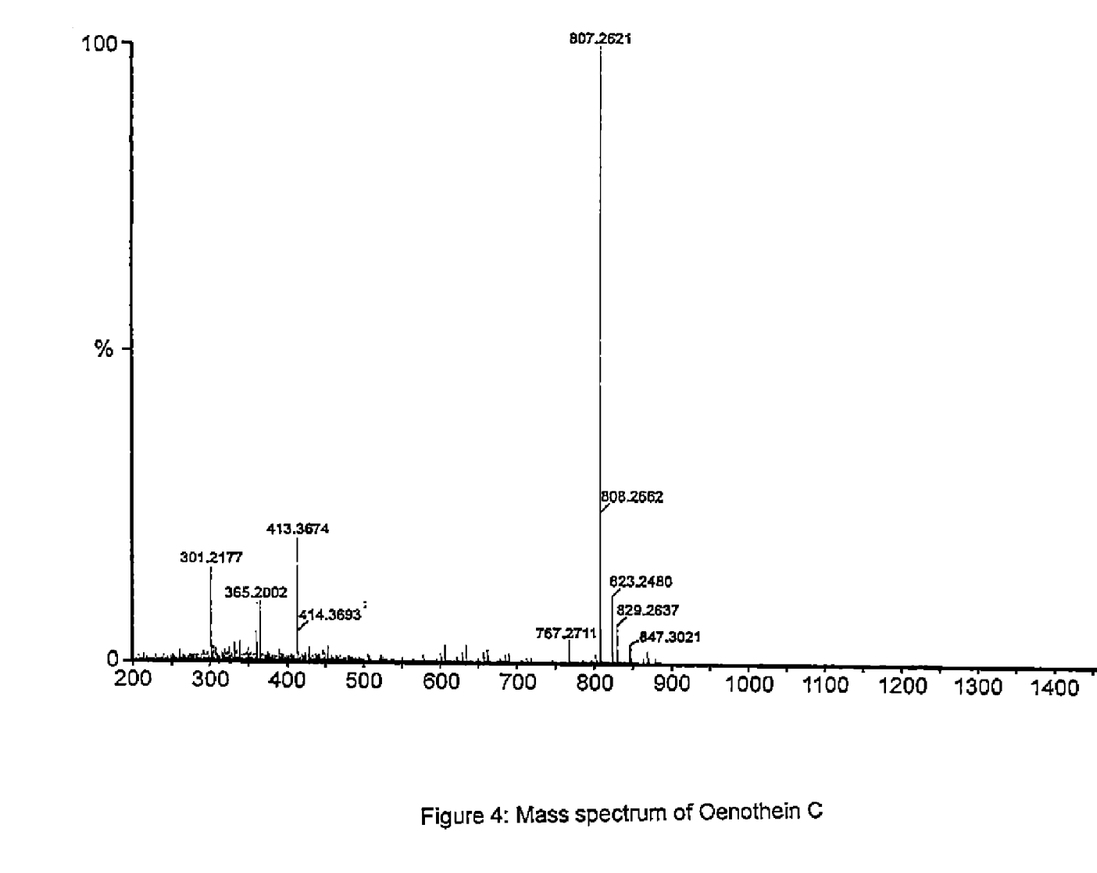
FIG. 4 represents the mass spectrum of the compound oenothein C.

The molecular weight was deduced to be 784 from its ESI-MS spectrum (sodiated molecular ion peak at m/z 807). Detailed analysis of $^1H$, $^{13}C$ and 2D-NMR spectra revealed the isolated compound to be a phenolic glycoside existing as an anomeric mixture (a and b). Literature study revealed two closely related structures: Oenothein C from *Oenothera erythrosepala* [54, 55] and its isomer from *Epilobium hirsutum* [56]. The 2D-NMR studies, in particular, confirmed the former possibility. The $[\alpha]_D$ of oenothein C was found to be +68° (literature value+72°). The systematic chemical nomenclature of oenothein C is: D-Glucose 2-[2-[(5,10-dihydro-3,7,8-trihydroxy-5,10-dioxo[1]benzopyrano[5,4,3-cde][1]benzopyran-2-yl)oxy]-3,4,5-trihydroxy benzoate]-3-(3,4,5-trihydroxybenzoate). The structure elucidations of various macrocyclic ellagitannins like woodfordins and oentheins are described in [54-58].

Table 1 shows anti gastric proton pump activity of oenothein C

Table 2 shows anti *H. pylori* activity of oenothein C and clarithromycin

Table 3 shows MIC and MBC values of oenotein C, clarithromycin, amoxicllin and metronidazole in different strains of *H. pylori*

DETAILED DESCRIPTION OF THE INVENTION

The molecule oenothein C has been isolated from the flowers of the plant *Woodfordia fruticosa*, abundantly available in the Indian subcontinent. Dried flowers of *Woodfordia fruticosa* were extracted by soaking overnight with 1:1 methanol-water at room temperature. The process was repeated thrice. The combined extract was evaporated at 45° C. in a rotary evaporator to get the crude extract. This was partitioned between n-butanol and water. The layers were separately evaporated at 45° C. to obtain two fractions. The n-butanol soluble fraction was chromatographed repeatedly over diaion HP-20 and sephadex LH-20 columns following bioassay guided fractionation technique to obtain pure oenothein C as an off-white solid, amorphous in nature. It is soluble in methanol, acetone and DMSO.

Figure 1A:
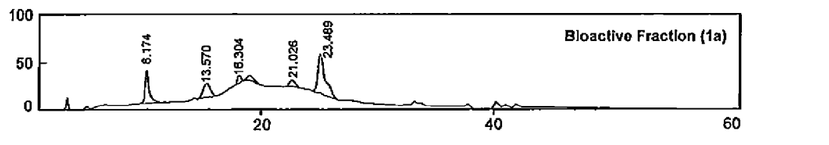
Figure 1B:
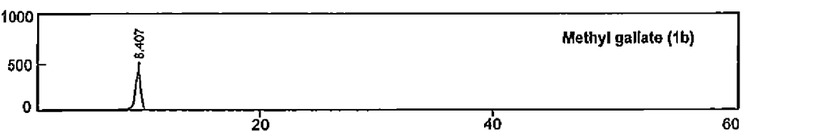
Figure 1C:
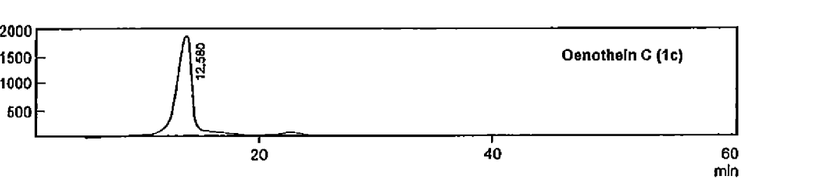

In HPLC, oenothein C showed a single peak corresponding to one of the major peaks in the crude extract. The HPLC profile of the crude extract is shown in FIG. 1(a). FIG. 1(c) shows the HPLC profile of the isolated single molecule, oenothein C. FIGS. 2, 3 and 4 represent NMR and Mass spectra of the compound oenothein C.

Figure 5:
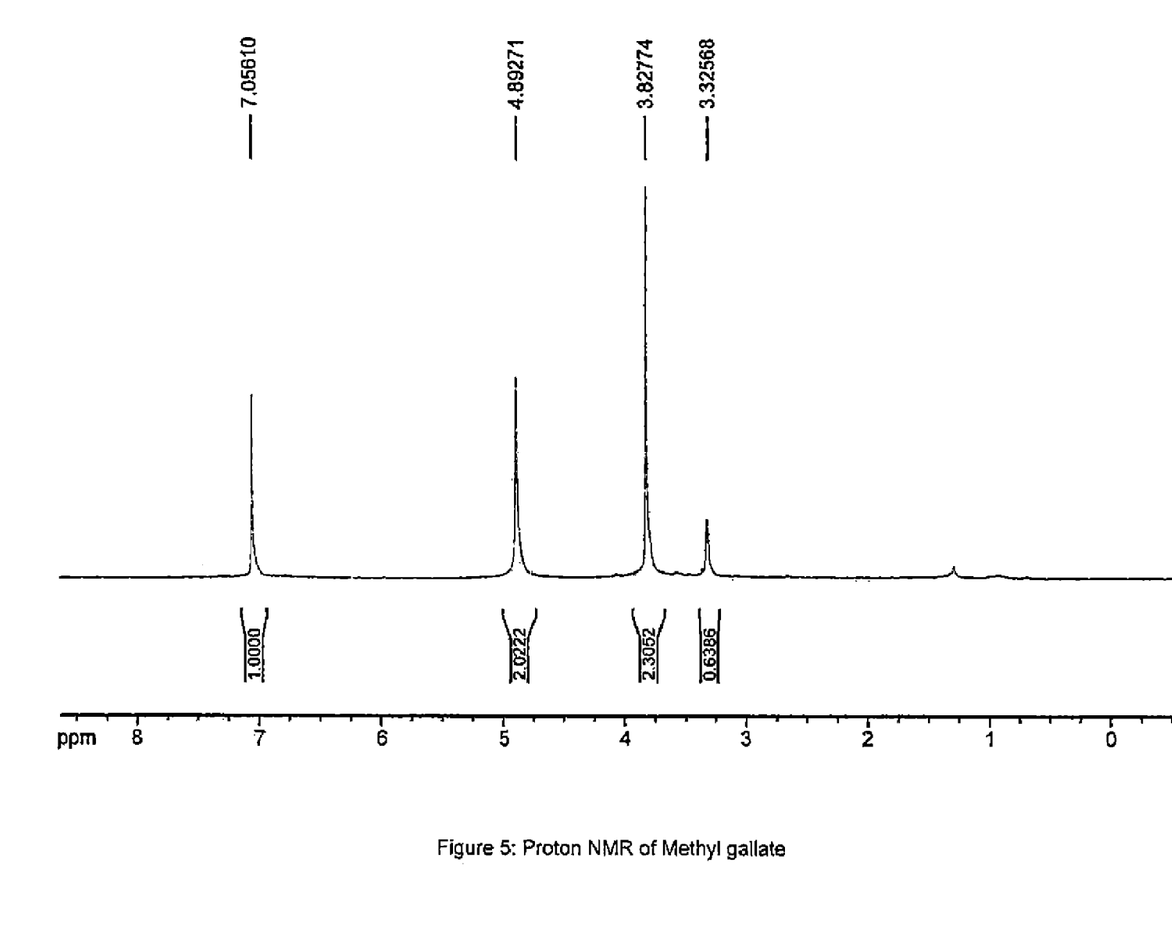
FIG. 5 represents the proton NMR of the compound methyl gallate.
Figure 6:
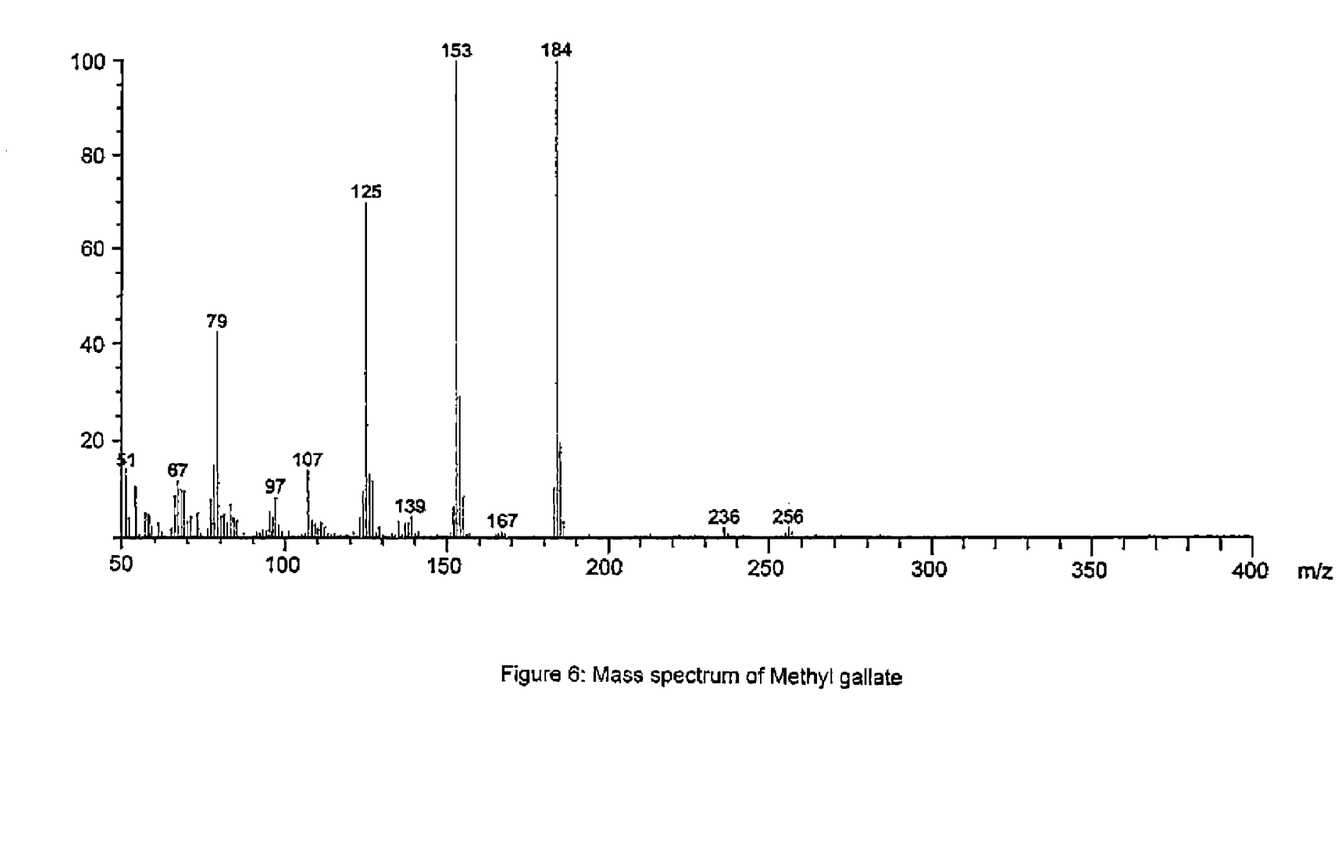
FIG. 6 represents the mass spectrum of the compound methyl gallate.
Figure 7:
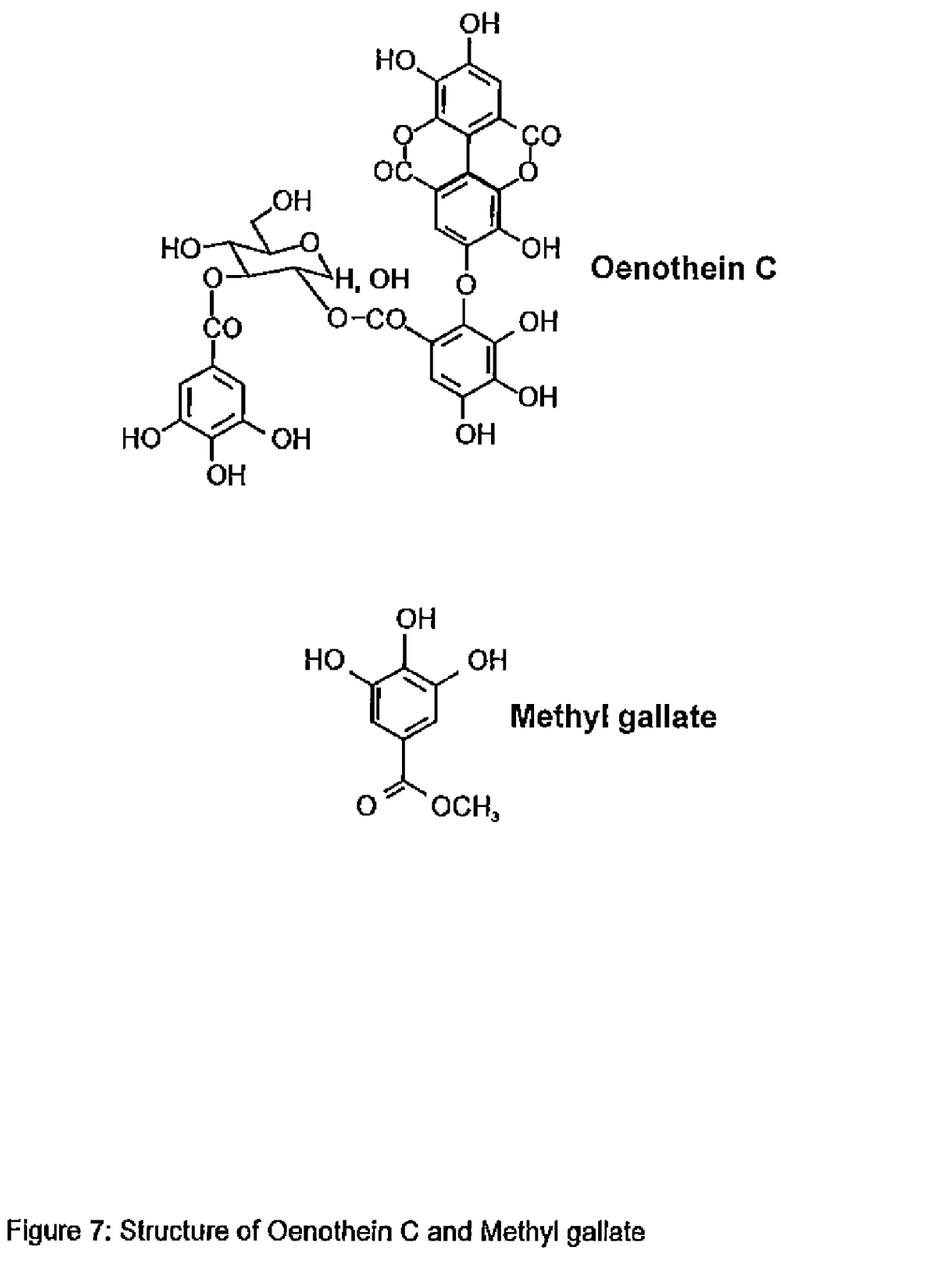
FIG. 7 represents the chemical structure of the compounds oenothein C and methyl gallate.

During fractionation by chromatography, another compound, methyl gallate was isolated. Its structure elucidated by $^1H$ NMR and ESI-Mass, then confirmed by comparing with a standard sample prepared in the laboratory. FIG. 1(b) shows its HPLC profile. The relative abundance (yield percent) of methyl gallate with respect to Bioactive Fraction was determined to 0.003%. FIGS. 5 and 6 respectively represent NMR and Mass spectra of the compound methyl gallate.

The compound methyl gallate however, did not show any activity, in any of the tests, described below. However this along with oenothein C will serve as the two fingerprint components in HPLC profile, in the final pharmaceutical preparation, from which one could judge the authenticity of the Bioactive Fraction. The two molecules, methyl gallate and oenthein C have been identified to delineate as the fingerprint component of the pharmaceutical preparation made from the bioactive fraction.

The following examples are given by way of illustration of the present invention and should not be construed to limit the scope of the present invention.

EXAMPLE-1

Isolation of Compounds Oenothein C and Methyl Gallate from the Plant *Woodfordia fructicosa*

The molecules oenothein C and methyl gallate have been isolated from the flowers of the plant *Woodfordia fruticosa*. Dried flowers of *Woodfordia fruticosa* were extracted by soaking overnight with 1:1 methanol-water at room temperature. The process was repeated thrice. The combined extract was evaporated at 45° C. in a rotary evaporator to get the crude extract. This was partitioned between n-butanol and water. The layers were separately evaporated at 45° C. to obtain two fractions. The n-butanol soluble fraction was chromatographed repeatedly over diaion HP-20 and sephadex LH-20 columns following bioassay guided fractionation technique to obtain pure oenothein C as an off-white solid, amorphous in nature (yield 0.008%). It is soluble in methanol, acetone and DMSO. The respective yield of methyl gallate was 0.003%.

EXAMPLE-2

Anti-Proton Pump Activity of Compound Oenothein C

Pig gastric membranes enriched in apical and tubulovesicular membranes were prepared according to [59]. Such membranes show $K^+$-stimulated $H^+$-transporting ATPase activity, which could be specifically blocked by omeprazole [60].

The $H^+,K^+$-ATPase activity was measured at 37° C. in a 1-mL reaction mixture containing 2 mM $MgCl_2$, 2 mM ATP, 10 mM PIPES (pH 6.8), 10 mM KCl and 10-12 µg membrane protein. An otherwise complete assay mixture was preincubated for 10 min in presence and absence of different concentrations of oenothein C or omeprazole before initiating the reaction with ATP. After incubation for 10 min, the reaction was terminated by the addition of 1 mL ice-chilled TCA (14%).

$K^+$-stimulated activity, referred to as $H^+,K^+$-ATPase, was calculated as the difference between the activity in presence of Mg plus $K^+$ and the basal activity ($Mg^+$-ATPase) in presence of $Mg^+$ alone. The membrane showed high $K^+$-stimulated activity of around 40-50 µmoles $p_i$/mg/h with basal activity of only around 10 µmoles $p_i$/mg/h. Following enzymatic assay method [61], the inhibitory activity of oenothein C was assessed. The effects are quantitated in terms of percent inhibition of $H^+,K^+$-ATPase, and compared with that of omeprazole, a specific inhibitor of gastric $H^+,K^+$-ATPase.

The molecule oenothein C showed extremely strong inhibition of gastric proton pump activity. At 1.3 µM, it produced about 70-90% inhibition of $H^+,K^+$-ATPase (Table 1) which is higher than the standard drug omeprazole (about 20% inhibition at 3 µM) when compared under identical experimental conditions. Thus, the degree of inhibition (ranging 20-90% at 0.13-1.30 µM) of the gastric proton pump with oenothein C is about 20-fold higher as compared with the standard medicine omeprazole (10-90% inhibition at 3-30 µM).

TABLE 1

| Anti gastric proton pump activity of oenothein C | | |
| --- | --- | --- |
| Molecule | Concentration (µM) | % Inhibition of $H^+, K^+$-ATPase |
| Oenothein C | 1.30 | 70-90 |
|  | 0.64 | 50-70 |
|  | 0.13 | 20-30 |
| Omeprazole | 30 | 80-90 |
|  | 15 | 40-60 |
|  | 3 | 10-30 |

EXAMPLE-3

Anti-*Helicobacter pylori* Activity of Compound Oenothein C

The effect of oenothein C for anti-Helicobacter pylori activity was examined using disc diffusion sensitivity assay as well as by determination of MIC/MBC values by microbroth dilution assay. Six different strains of *H. pylori*, of which 2 are clinical strains [80A (avirulent) and 121A (virulent)] and four standard strains [ATCC 43504, ATCC 49503, NCTC 26695 and ATCC 43629], were maintained at 37° C. incubator under appropriate conditions (10% $CO_2$, 5% $O_2$, 85% $N_2$ and >95% relative humidity). The molecule oenothein C was dissolved in DMSO.

For Disc diffusion sensitivity assay [62], the culture plates were made with Brain Heart Infusion Agar supplemented with 10% fetal calf serum (FCS), Isovitalex (0.5%) and Dent (0.0025%). The plates were flooded with $1 \times 10^6$ CFU/mL of liquid cultures of *H. pylori*, the discs were placed on the plate and the sample was impregnated directly on the disc at a dose of 54/disc or 10 µL/disc so as to give 100 µg/disc and 200 µg/disc. After 3 days of incubation, the inhibition zone diameter was measured and compared to that with standard antibiotic clarithromycin.

The molecule oenothein C produced inhibition zone diameter ranging 1.7-2.5 cm at the dose range of 100-200 µg/disc when examined against 6 different strains of *H. pylori*. The activities with clarithromycin, standard antibiotics, were determined under similar experimental conditions (Table 2).

TABLE 2

| Anti *H. pylori* activity of oenothein C and clarithromycin | | | | | | | |
| --- | --- | --- | --- | --- | --- | --- | --- |
| | | Inhibition Zone Diameter (cm) | | | | | |
| Sample | Concentration (µg/disc) | 80A | 121A | ATCC 43504 | ATCC 49503 | NCTC 26695 | ATCC 43629 |
| Oenothein C | 100 | 2.0 | 1.7 | 2.0 | 1.7 | 2.0 | 1.9 |
|  | 200 | 2.5 | 2.0 | 2.7 | 2.2 | 2.4 | 2.3 |
| Clarithromycin* | (ng/disc) | 1.8 (10) | 1.8 (10) | 2.0 (40) | 1.7 (5) | 2.0 (400) | 1.7 (100) |

For clarithromycin, the values in bracket indicate concentrations used with respective strains.

For the determination of MIC and MBC values by microbroth dilution assay [63], a two-fold serial dilution (ranging between 1-50 µg/mL) of oenothein C was prepared in a 96-well microtitre plate containing a total volume of 100 µL of *Brucella* broth supplemented with 5% FCS. A 3-day liquid culture of *H. pylori* was diluted 10-times in *Brucella* broth and 100 µL of these cultures were inoculated into each well to give a final concentration of ~$10^6$ CFU/mL. The plates were incubated for 3 days in a microaerophilic atmosphere at 37° C. Following incubation, the plates were examined visually, and the lowest concentration showing complete inhibition of growth was recorded as the MIC of the respective compound. For MBC determination, aliquots (10 µL) of 72-h culture in which no growth had been detected were taken from the wells of the above microtitre plates and used to streak on fresh brain heart infusion agar plates. MBCs were determined by visual inspection of such plates after further incubation for 72 h at 37° C. and the point where no growth (less than 10 colony) appeared was considered as the MBCs. Standard antibiotics clarithromycin, amoxycillin and metronidazole were included for comparison with oenothein C employing different strains of *H. pylori*.

The MIC and the MBC values of the molecule oenothein C were determined against five strains by microbroth dilution assay. With strains 80A, ATCC 43504, ATCC 49503, NCTC 26695 and ATCC 43629, the observed MIC values were 25, 25, 6.25, 12.5, and 25 µg/mL respectively (Table 3). The MIC values of clarithromycin under identical experimental conditions have been 20, 25, 6.25, 62.5, and 50 ng/mL for the respective strains. Likewise, the MIC values of amoxycillin employing such strains were observed to be 20, 25, 12.5, 100, and 25 ng/mL respectively. Based on MIC values against different strains, the molecule oenothein C appears to be about 500-1000 fold less potent as compared with clarithromycin and amoxycillin both. However, in respect of metronidazole MIC values (12.5, 50, 1.56, 1.56 and 1.56 µg/mL), oenothein C is just about 2-20 fold less competent as observed in 5 such strains. In terms of MBC values, a measure of bactericidal activity, similar trend in efficacy of oenothein C vis-à-vis the three standard antibiotics was noted.

To summarize, the efficacy of the molecule oenothein C against different strains, clinical as well as standard, is evident. Further, since some of the strains are toxin producing (cag-A, vac-A, cytotoxin positive), the molecule is expected to show efficacy against such strains under pathogenic conditions.

Further, the antibacterial activity of oenothein C was examined against four aerobic bacteria (1 gram positive, *B. cereus* and 3 gram negative, *S. typhi, E. coli* & *K. pneumoniae*) by microbroth dilution assay in Muller Hinton broth essentially by following NCCLS (National Commmittee for Clinical Laboratory Standards) guideline [64]. The molecule oenothein C showed no activity against any of the bacterial strains (MIC>400 µg/mL). Hence the compound is specific against *H. pylori*.

EXAMPLE-4

Toxicity Evaluation for the Compound Oenothein C

The compound oenothein C was checked for mortality of the Swiss albino mice.

Maximum dosage of 250 mg/Kg body weight of compound oenothein C was given to 5 swiss albino mice via oral route. After 24 hours, it was seen that there is no mortality in any of the mice. Further, the mice were kept under observation for 15 days, during which period they were found to remain healthy, and no behavioral abnormality were noted.

Advantages:
1. The inhibition of gastric proton pump by the compound oenothein C is much stronger than standard medicine omeprazole (about 20 times).
2. Reasonably low MIC values (6.25-25.0 µg/mL) of the same molecule oenothein C against clinical and different standard strains of *H. pylori* has also been provided in the present invention.
3. The specific anti *H. pylori* activity of the molecule oenothein C is evident from its high MIC values (>400 µg/mL) against a panel of aerobic bacteria, suggesting its potential as a useful therapeutic agent.
4. Since the acid HCl and the bug *H. pylori* are the two major reasons for the pathogenesis of gastroduodenal ulcers, position of oenothein C as a single molecule anti gastric and duodenal ulcer medicine is unique. This is more because of the failure of the current medical management even after using triple therapy and also quadruple therapy (clarithromycin, amoxycillin, proton pump inhibitor, $H_2$ receptor blocker, sucralfate—any 3 or 4 depending on the diagnosis and other criteria) in terms of ulcer recurrence and antibiotic resistance.

TABLE 3

MIC and MBC values of oenotein C, clarithromycin, amoxicllin and metronidazole in different strains of *H. pylori*

| | MIC (µg/ml) | | | | | MBC (µg/ml) | | | | |
| --- | --- | --- | --- | --- | --- | --- | --- | --- | --- | --- |
| Sample | 80A | ATCC 43504 | ATCC 49503 | NCTC 26695 | ATCC 43629 | 80A | ATCC 43504 | ATCC 49503 | NCTC 26695 | ATCC 43629 |
| Oenothein C | 25 | 25 | 6.25 | 12.5 | 25 | 50 | >50 | 50 | 25 | >50 |
| Clarithromycin | 0.02 | 0.025 | 0.006 | 0.063 | 0.050 | 0.04 | 0.05 | 0.013 | 0.1 | 0.1 |
| Amoxycillin | 0.02 | 0.025 | 0.013 | 0.1 | 0.025 | 0.08 | 0.05 | 0.05 | <1.0 | 0.05 |
| Metronidazole | 12.5 | 50 | 1.56 | 1.56 | 1.56 | >100 | 100 | 12.5 | 10 | 6.25 |

REFERENCE

[1] Rogers, A. I. 1990. Postgrad Med. 88, 57-60.

[2] Lee A. 1996. In *Helicobacter pylori*: Techniques for Clinical Diagnosis & Basic Research (Eds. Adrian Lee & Francis Megraud), WB Saunders Co. Ltd., London, pp. xiii-xiv.

[3] Hoogerwerf, W. A. and Pasricha, P. J. In Goodman & Gilman's Pharmacological Basis of Therapeutics (Eds. Hardman, J. G. & Limbird, L. E.) McGraw-Hill 2001, pp 1005-1020.

[4] Bullard, W. Peptic Ulcer Diseases, US National Community Pharmacists Association, June 1997.

[5] Das, P. K., Sahu, N. P., Banerjee, S., Sett, S., Goswami, S., Bhattacharya, S., 2003. PCT (WO 03/080095 [PCT/IN/03/0067]) & US Patent Application 20060040005.

[6] Shome, U., Mehrotra, S., Sharma, H. P., 1981. Proceedings of Indian Academy of Sciences (Plant Science) 90, 335-351.

[7] Khare, C. P., 2004. Encyclopedia of Indian Medicinal Plants: Rational Western Therapy, Ayurvedic and Other Traditional Usage, Botany. Springer, Berlin, pp. 483-484.

[8] Kirtikar, K. R., Basu, B. D., 1935. Indian Medicinal Plants. Parts 1-3, L. M. Basu, Allahabad, India.

[9] Central Council for Research in Indian Medicine and Homeopathy. (1978) *Hand Book of Domestic Medicine and Common Ayurvedic Remedies*, Ministry of Health and Family Welfare, New Delhi, pp. 334-35.

[10] Krishnan, P. N., Seeni, S., 1994. Plant Cell Reports 14, 55-58.

[11] Chopra, R. N., Nayar, S. L., Chopra, I. C., 1956. Glossary of Indian Medicinal Plants (CSIR, Delhi, India).

[12] Watt, G., 1972. A Dictionary of Economic Products of India III. (Periodical Expert, Shandara, Delhi, India).

[13] Dymock, W., Warden, C. J. H., Hooper, D., (1995). A History of the Principal Drugs of Vegetable Origin met within British India Republic. Pharmacographia Indica. Vol. I (Vivek Vihar, Delhi, India).

[14] Oudhia, P., 2003. Interaction with the herb collectors of Gandai region, Chhatisgarh, M. P. India. www.botanical.com.

[15] Sharma, P. V., 1956. Dravyagun Vigyan (Varanasi: The Chowkhamba).

[16] Dutt, U. C., 1922. The Materia Medica of the Hindus. Adi Ayurveda Machine Press, Kolkata, India.

[17] Nadkarni, K. M., 1954. Indian Materia Medica vol. 2, $3^{rd}$ Edin. Popular Book Depot, Mumbai, India, pp. 489-497.

[18] Ahuja, B. S., 1965. Medicinal Plants of Saharanpur. Gurukul Kangri Printing Press, Hardwar, India.

[19] Atal, C. K., Bhatia, A. K., Singh, R. P., 1982. Journal of Research in Ayurveda and Siddha III (3 & 4), 193-199.

[20] Jayaweera, D. M. A., 1981. Medicinal Plants used in Ceylon Part III (The National Science Council of Sri Lanka, Colombo) p. 289.

[21] Weersaooiya, M. K. B., Yatawara, H. P., 2002. Indian Journal of Biochemistry and Biophysics 39, 347-350.

[22] Burkill, I. H., 1966. A Dictionary of Economic Products of the Malay Peninsula. (Ministry of Agriculture and Co-operatives, Kualalampur) p. 2305.

[23] Dey, K. L., 1984. The Indigenous Drugs of India. International Book Distributors, Dehradun, India, p. 311.

[24] Deshmukh, V. K., Pandit, U., 1967. Indian Journal of Pharmacy 29, 341.

[25] Chauhan, J. S., Srivastava, S. K., Srivastava, S. D., 1979. Planta Medica 36, 183-184.

[26] Dan, S., Dan, S. S., 1984. Journal of the Indian Chemical Society 61, 726-727.

[27] Kalidhar, S. B., Parthasarathy, M. R., Sharma, P., 1981. Indian Journal of Chemistry 20B, 720-721.

[28] Dastur, J. F., 1951. Medicinal Plants of India and Pakistan, Taraporevala Sons & Co. Ltd., Mumbai, India.

[29] Saoji, A. G., Saoji, A. N., Deshmukh, V. K., 1972. Current Science 41, 192.

[30] Nair, A. G. R., Kotiyal, J. P., Ramesh, P., Subramanian, S. S., 1976. Indian Journal of Pharmacy 38, 110-111.

[31] Yoshida, T., Chou, T., Haba, K., Okano, Y., Shingu, T., Miyamoto, K., Koshiura, R., Okuda, T., 1989. Chemical and Pharmaceutical Bulletin 37, 3174-3176.

[32] Yoshida, T., Chou, T., Nitta, A., Miyamoto, K., Koshiura, R., Okuda, T., 1990. Chemical and Pharmaceutical Bulletin 38, 1211-1217.

[33] Kadota, S., Takamori, Y., Nyein, K. N., Kikuchi, T, Tanaka, K., Ekimoto, H., 1990. Chemical and Pharmaceutical Bulletin 38, 2687-2697.

[34] Yoshida, T., Chou, T., Matsuda, M., Yasuhara, T., Yazaki, K., Hatano, T., Nitta, A., Okuda, T., 1991. Chemical and Pharmaceutical Bulletin 39, 1157-1162.

[35] Ayurvedic Pharmacopoeia 1976; 1979. Department of Ayurveda, Colombo Sri Lanka. Vol I pt. 1 and 2.

[36] Kroes, B. H., Van-den Berg, A. J. J., Abeysekera, A. M., de Silva, K. T. D., Labadie, R. P., 1993. Journal of Ethnopharmacology 40, 117-125.

[37] Anonymous: The Ayurvedic Formulary of India, 1978. Ministry of Health and Family Planning, New Delhi, India, Part I.

[38] Alam, M., Shanmuga Dasan, K. K., Thomas, S., Suganthan, J., 1998. Ancient Science of Life 17, 305-312.

[39] Biswas, K. P., Ghosh, A. K., 1951. Bharatiya Bonousadhi, Calcutta University Press, Kolkata, India, pt. 1, p. 67.

[40] Tewari, P. V., Neelam, Kulkarni, K. S., 2001. Ancient Science of Life XXI, 139-149.

[41] Kuramochi-Motegi, A., Kuramochi, H., Kobayashi, F., Ekimoto, H., Takahashi, K., Kadota, S., Takamori, Y., Kikuchi, T., 1992. Biochemical Pharmacology 44, 1961-1965.

[42] Wang, C. C., Chen, L. G., Yang, L. L., 1999. Cancer Letters 140, 195-200.

[43] Miyamoto, K., Nomura, M., Murayama, T., Furukawa, T., Hatano, T., Yoshida, T., Koshiura, R., Okuda, T., 1993. Biological and Pharmaceutical Bulletin 16, 379-387.

[44] Liu, M. J., Wang, Z., Li, H. X., Wu, R. C., Liu, Y. Z., Wu, Q. Y., 2004. Toxicology and Applied Pharmacology 194, 141-155.

[45] Chen, Y.-C., Yang, L.-L., Lee, T. J-F., 2000. Biochemical Pharmacology 59, 1445-1457.

[46] Jianmin, Y, Chengqi, F, Lei, D, Yan, W, Bingjun, R WO/2004/045631 PCT/CN2003/000988.

[47] Kim, D-H, Bae, E-A, Han, M-J, Choo, M-K, Park, E-K, Park, J-H US Patent application 20030190377.

[48] Pushpangadan, P., Venketeswararao C., Govindarajan, R, Mehrotra, S., Nair, R K US Patent Application 20040121029.

[49] Miyazaki, T., Kosaka, K., Ito, H. U.S. Pat. No. 6,638,523.

[50] Katiyar, C. K., Duggal, R. K., Rao, B. V. J. U.S. Pat. No. 6,455,077

[51] Gourvest, J-F., Kasal, A., Lesuisse, D., Teutsch, J-G. U.S. Pat. No. 5,525,594.

[52] Muthuswamy, M. P., WO/2003/055558 PCT/IN2002/000041

[53] Tsuneo, N., Yukio, H., Kenji, S., Saori, T. Japan Patent JP 07126144.

[54] Yoshida, T., Chou, T., Nitta, A., Okuda, T., 1992. Chemical and Pharmaceutical Bulletin 38, 2023-2030.

[55] Hatano, T., Yasuhara, T., Matsuda, M., Yazaki, K., Yoshida, T. Okuda, T., 1990. Journal of Chemical Society Perkin Transactions 1, 2735-2743.

[56] Hatano, T., Ogawa, N., Kira, R., Yasuhara, T., Okuda, T., 1989. Chemical and Pharmaceutical Bulletin 37, 2083-2090.

[57] Barakat, H. H., Hussein, S. A. M., Marzouk, M. S., Merfort, I., Linscheid, M., Nawwar, M. A. M., 1997. Phytochemistry 46, 935-941.

[58] Okuda, T., Yoshida, T., Hatano, T. 1995. Hydrolyzable tannins and related polyphenols. In: Herz, W., Kirby, G. W., Moore, R. E., Steglich, W., Tamm, C. (Eds.) Progress in the chemistry of organic natural products, vol. 66. Springer-Verlag, Wien, N.Y. pp 1-117.
[59] Bandopadhyay, S, Das, P. K., Wright, M. V., Nandi, J., Bhattacharya, D. and Ray, T. K., 1987. Journal of Biological Chemistry 262, 5664-5670.
[60] Sachs, G., Carlsson, E., Lindberg, P., Wallmark, B. 1988. Ann. Rev. Pharmacol. Toxicol. 28, 269-284.
[61] Sanui, H.1974. Analytical Biochemistry 60, 489-504.
[62] Glupczynski, Y. 1996. In *Helicobacter pylori*: Techniques for Clinical Diagnosis & Basic Research (Eds. Adrian Lee & Francis Megraud), WB Saunders Co. Ltd., London pp. 17-32.
[63] Hachem, C. Y., Clarridge, J. E., Reddy, R, Flamm, R., Evans, D. G., Tanaka, S. K., Graham, D. G. 1996. Diagnostic Microbiology and Infectious Diseases 24, 37-41.
[64] Baron, E. J., Peterson, L. R. and Finegold, S. M. In Bailey & Scott's Diagnostics Microbiology, 4th ed., chapter 14, Mosley-Year Book, Inc., 1994, pp 168-188.

The invention claimed is:
1. A method for treating peptic ulcer disease in a subject, comprising administering a pharmaceutical composition consisting essentially of a therapeutically effective amount of oenothein C.
2. A method for inhibiting *Helicobacter pylori* in a subject having peptic ulcer disease, comprising administering a pharmaceutical composition consisting essentially of a therapeutically effective amount of oenothein C.
3. The method of any one of claim 1 or 2, wherein the said oenothein C is administered at a dose of 0.005 mg/Kg body weight/day to 0.5 mg/Kg body weight/day.
4. The method of any one of claim 1 or 2, wherein the said oenothein C is administered at a dose of at least 0.05 mg/Kg body weight/day.
5. The method of any one of claim 1 or 2, wherein the said oenothein C does not show any toxic effect at the single dose level up to 250 mg/kg body weight.
6. The method of any one of claim 1 or 2, wherein the peptic ulcer disease is selected from the group consisting of gastric ulcer, duodenal ulcer and also gastritis, gastro esophageal reflux disorder (GERD).
7. The method of any one of claim 1 or 2, wherein the oenothein C inhibits gastric proton pump activity in vitro in the concentration range from 0.13 to 1.3 µM wherein the IC50 value is 0.6 to 0.8 µM.
8. The method of any one of claim 1 or 2, wherein the oenothein C shows bacteriostatic and bactericidal activity against clinical and standard strains of *Helicobacter pylori*.
9. The method of any one of claim 1 or 2, wherein the oenothein C shows bacteriostatic activity against *Helicobacter pylori* with a minimum inhibitory concentration (MIC) in the range of 6.25 µg/mL to 25.0 µg/mL.
10. The method of any one of claim 1 or 2, wherein the oenothein C shows a bactericidal activity against *Helicobacter pylori* with minimum bactericidal concentration (MBC) in the range of 25.0 µ/mL to 50.0 µ/mL.
11. The method of any one of claim 1 or 2, wherein the oenothein C is administered orally, intramuscularly, or intravenously.
12. The method of any one of claim 1 or 2, wherein the oenothein C is administered as a pharmaceutically acceptable powder, injectable, syrup, capsule or tablet.
13. The method of any one of claim 1 or 2, wherein the pharmaceutical composition further includes a pharmaceutically acceptable carrier, excipient, diluent or solvent, wherein said carrier is a protein, a carbohydrate, a sugar, magnesium stearate, cellulose, calcium carbonate, or a starch-gelatin paste.

* * * * *